(12) United States Patent
Sun

(10) Patent No.: US 11,774,440 B2
(45) Date of Patent: Oct. 3, 2023

(54) METHOD FOR DETECTING CHEMOTAXIS OF NEUTROPHIL

(71) Applicant: SUZHOU MUNICIPAL HOSPITAL, Suzhou (CN)

(72) Inventor: Bingwei Sun, Suzhou (CN)

(73) Assignee: SUZHOU MUNICIPAL HOSPITAL, Suzhou (CN)

(*) Notice: Subject to any disclaimer, the term of this patent is extended or adjusted under 35 U.S.C. 154(b) by 0 days.

(21) Appl. No.: 18/124,577

(22) Filed: Mar. 22, 2023

(65) Prior Publication Data

US 2023/0228735 A1    Jul. 20, 2023

Related U.S. Application Data

(63) Continuation-in-part of application No. PCT/CN2020/117066, filed on Sep. 23, 2020.

(51) Int. Cl.
*G01N 33/49* (2006.01)
*G01N 33/50* (2006.01)

(52) U.S. Cl.
CPC ....... *G01N 33/491* (2013.01); *G01N 33/5029* (2013.01)

(58) Field of Classification Search
CPC .......... G01N 33/491; G01N 33/5029
See application file for complete search history.

(56) References Cited

FOREIGN PATENT DOCUMENTS

| CN | 109971819 A | 7/2019 |
|----|-------------|--------|
| JP | 10227792 A  | * 8/1998 |

* cited by examiner

*Primary Examiner* — Terry K Cecil
(74) *Attorney, Agent, or Firm* — SOROKER AGMON NORDMAN PTE LTD

(57) ABSTRACT

Disclosed is a method for detecting chemotaxis of neutrophil, including: mixing a blood sample and an equal volume of glucose, mixing, and standing; taking a supernatant of the blood sample after standing into a centrifuge tube, and centrifuging; adding 1× calcium and magnesium ion-free HBSS into a centrifuged blood sample to re-suspend cell aggregates at bottom; uniformly blowing and dispersing a re-suspended bottom cell aggregates, and slowly adding a polysucrose solution from the bottom of the centrifuge tube to perform density gradient centrifuging treatment; dividing a density gradient centrifuged solution into three layers, pipetting a clear liquid at an upper layer and a PBMC layer at a middle layer to obtain cell aggregates at a bottom layer; lysing erythrocytes in the cell aggregates, then successively adding 2× calcium and magnesium ion-free HBSS and 1× calcium and magnesium ion-free HBSS, mixing, and centrifuging again to obtain neutrophils.

6 Claims, 2 Drawing Sheets

METHOD FOR DETECTING CHEMOTAXIS OF NEUTROPHIL

RELATED APPLICATION

The application claims priority as a continuation-in-part application under 35 U.S.C. 111(2) from International Application No. PCT/CN2020/117066 filed on 23 Sep. 2020, which is incorporated by reference as if fully-set forth herein.

FIELD OF TECHNOLOGY

The present disclosure relates to a method for detecting chemotaxis of neutrophil.

BACKGROUND

Neutrophils are important innate immune cells that resist an invasion of pathogens in human body. They are produced by bone marrow hematopoietic stem cells, differentiated and developed in bone marrow, and enter blood or tissue. They are the largest number of white blood cells in peripheral blood of the body, accounting for 40% to 75% of the total number of white blood cells under normal physiological state. In Wright stained blood smear, the cytoplasm of the neutrophils is colorless or very light pink, the nuclei are rod-shaped or lobulation-shaped with 2 to 5 lobulations, and there are filaments between the lobulations, therefore, they are often called polymorphonuclear leukocytes (PMNs), which have chemotactic, phagocytic and bactericidal functions. When the human body is invaded by pathogenic bacteria, neutrophils can chemotactic move to an infection site, engulf the bacteria into the cells, and kill the bacteria through a variety of ways. They are the first line of defense against bacterial infection and play a very important role in the human non-specific immune system.

In recent years, many studies at home and abroad have shown that various diseases such as infections, severe diseases, tumors and diabetes are closely related to neutrophils, wherein the abnormal chemotaxis of neutrophils in patients makes it impossible for neutrophils to reach the site of infection to remove pathogenic microorganisms, and excessive neutrophils recruited to non-inflammatory sites will cause organ damage. Therefore, the detection and analysis of chemotactic function of neutrophil provides a new orientation for accurate diagnosis and treatment of the immune status of patients, and has very important clinical significance.

BRIEF SUMMARY

One aspect of the present disclosure relates to a method for detecting chemotaxis of neutrophil, which can save the time of neutrophil extraction and can detect the chemotactic function of extracted neutrophils.

One aspect of the present disclosure provides a method for detecting chemotaxis of neutrophil, which comprises the following steps:

i, collecting a blood sample into an Ethylenediaminetetraacetic acid (EDTA) anticoagulant tube, adding an equal volume of glucose, mixing, and standing;

ii, taking a supernatant of the blood sample after standing into a centrifuge tube, and centrifuging;

iii, adding 1× calcium and magnesium ion-free Hank's balanced salt solution into a centrifuged blood sample to re-suspend cell aggregates at bottom;

iv, uniformly blowing and dispersing a re-suspended bottom cell aggregates, and slowly adding a polysucrose solution from the bottom of the centrifuge tube to perform density gradient centrifuging treatment;

v, dividing a density gradient centrifuged solution into three layers, pipetting a clear liquid at an upper layer and a peripheral blood mononuclear cell (PBMC) layer at a middle layer to obtain cell aggregates at a bottom layer;

vi, lysing erythrocytes in the cell aggregates by using sterile water, gently blowing and sucking, then successively adding 2× calcium and magnesium ion-free Hank's balanced salt solution and 1× calcium and magnesium ion-free Hank's balanced salt solution, mixing, and centrifuging again to obtain neutrophils; and vii, counting the neutrophils, adjusting concentration of the neutrophils, and pipetting a neutrophil suspension into a chemotactic model to chemotactic move.

In one embodiment, step ii specifically comprises:
letting the blood sample stand still at room temperature for 20 minutes, taking the supernatant of the blood sample into the centrifuge tube, and centrifuging the supernatant at a centrifugal force of 400 g and 20° C. for 10 minutes.

In one embodiment, in step iv, the density gradient centrifuging treatment specifically comprises:
centrifuging at a centrifugal force of 400 g and 20° C. for 35 minutes.

In one embodiment, the erythrocytes in the cell aggregates need to be lysed twice.

In one embodiment, in step vi, the centrifuging again specifically comprises:
centrifuging at a centrifugal force of 400 g and 20° C. for 7 minutes.

In one embodiment, the chemotaxis model is a culture dish, and the culture dish is a transparent culture dish to observe a migration of neutrophils.

The beneficial effects of the present disclosure are that through the centrifugation and lysis of the blood sample, neutrophils can be quickly extracted, the extraction speed is improved, and the detection time is shortened. The method is simple, efficient and fast, and the extracted neutrophils have improved properties.

DETAILED DESCRIPTION OF EXEMPLARY EMBODIMENTS

Figure 1:
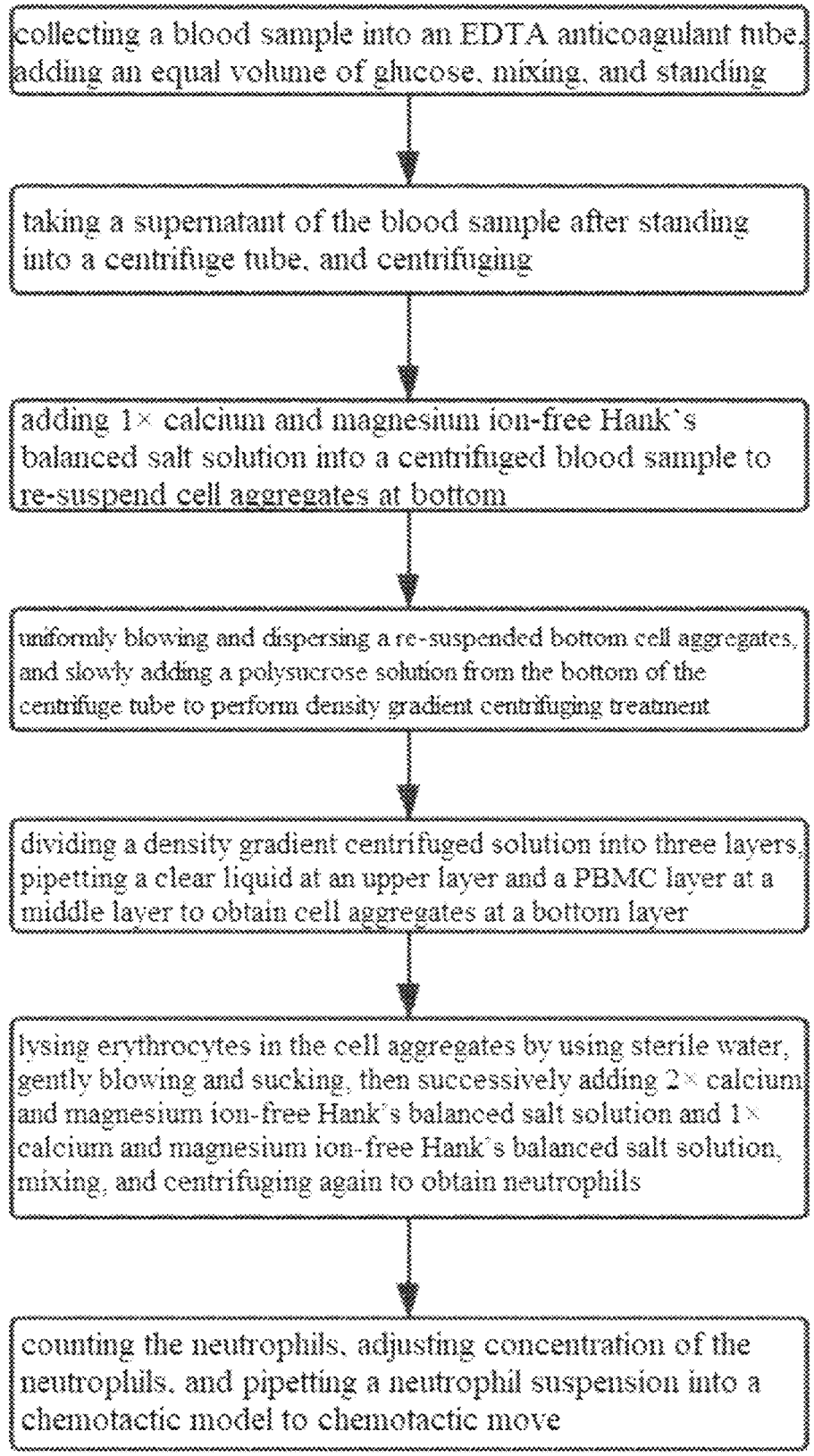
FIG. 1 is a flow chart of a method for detecting chemotaxis of neutrophil according to an embodiment of the present disclosure.

Referring to FIG. 1, a method for detecting chemotaxis of neutrophil in a preferred embodiment of the present disclosure, includes the steps i to vii.

Step i, collect a blood sample into an EDTA anticoagulant tube, add an equal volume of glucose, mix well, and stand still. In this embodiment, the color of the EDTA anticoagulant tube was purple, the volumes of blood sample and the glucose were 2 ml, and the concentration of glucose was 3%. Of course, in other embodiments, there can also be other volumes of the blood sample and glucose, and there can also be other concentrations of glucose, which are not specifically limited, and depend on the actual situation.

Step ii, take the supernatant of the blood sample after standing into a centrifuge tube, and perform centrifugation. Specifically, let the blood sample stand at room temperature for 20 minutes, taking the supernatant into the centrifuge tube, and centrifuging the supernatant at a centrifugal force of 400 g and 20° C. for 10 minutes. Of course, in other embodiments, there can also be other centrifugation conditions, which is no specifically limited, and depend on the actual situation.

Step iii, add 1× calcium and magnesium ion-free Hank's balanced salt solution (HBSS) into the centrifuged blood sample to re-suspend cell aggregates at the bottom. Wherein, the 1× calcium and magnesium ion-free Hank's balanced salt solution was a pre-prepared stock solution, at this time, the stock solution was not required to be diluted, and can be directly added to the centrifuged blood sample. In the above description, the volume of the 1× calcium and magnesium ion-free Hank's balanced salt solution was 3 ml.

Step iv, uniformly blow and disperse the re-suspended bottom cell aggregates, and slowly add a polysucrose solution from the bottom of the centrifuge tube to perform density gradient centrifuging treatment. The density gradient centrifuging treatment specifically is, performing centrifugation at a centrifugal force of 400 g and 20° C. for 35 minutes.

Step v, divide the density gradient centrifuged solution into three layers, pipet the clear liquid at the upper layer and the PBMC layer at the middle layer to obtain cell aggregates at the bottom layer. Wherein, the PBMC layer was a peripheral blood mononuclear cell layer, and contained a large number of monocytes and lymphocytes, and the bottom was red blood cells and mature neutrophils.

Step vi, lyse erythrocytes in the cell aggregates by using sterile water, and in this embodiment, the erythrocytes in the cell aggregates needed to be lysed twice, and the volume of the sterile water was 3 ml. Gently blow and suck, then successively add 2× calcium and magnesium ion-free Hank's balanced salt solution and 1× calcium and magnesium ion-free Hank's balanced salt solution, mix well, and performing centrifuging treatment again to obtain neutrophils; performing centrifuging treatment again specifically is: performing centrifugation at a centrifugal force of 400 g and 20° C. for 7 minutes. 2× calcium and magnesium ion-free Hank's balanced salt solution is calcium and magnesium ion-free Hank's balanced salt solution with 2 times osmotic pressure.

Figure 2:
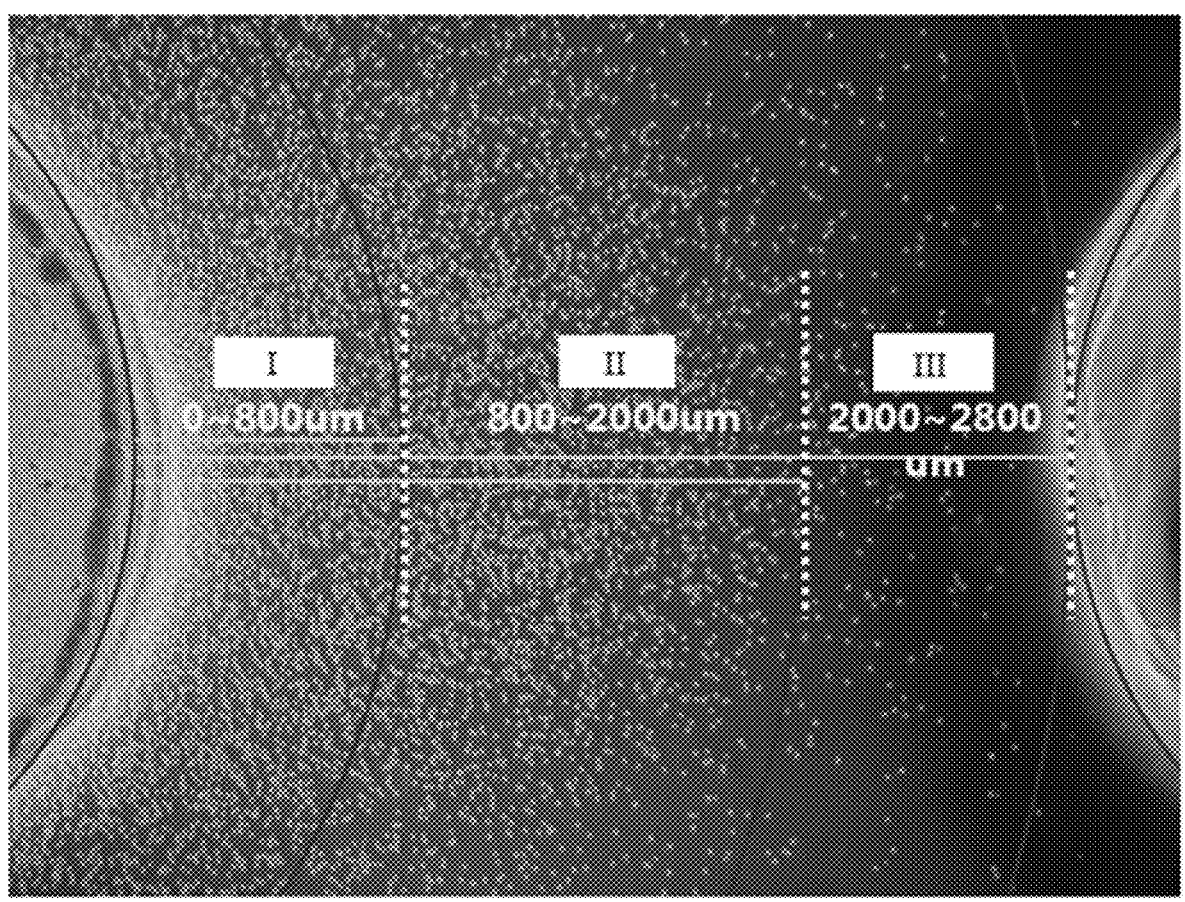
FIG. 2 is a schematic diagram of chemotactic movement of the neutrophils extracted according to an embodiment of the present disclosure.

Step vii, as shown in FIG. 2, count the neutrophils, adjust the concentration of the neutrophils, and pipet the neutrophil suspension into a chemotactic model to chemotactic move. The chemotactic model was a culture dish, and the culture dish was a transparent culture dish to visually observe the migration of neutrophils. Specifically, the culture dish was the device for cell transmigration assay and the forming mould for manufacturing the device disclosed by the Chinese patent CN105062865 B, which is not described here.

The time required for conventional extraction of neutrophils is about 2 hours. The time required to extract neutrophils according to the above method was doubled faster, and the steps are simplified to achieve the effects of improving the extraction speed and shortening the detection time.

As shown in FIG. 2, as shown by the final chemotaxis test results, the chemotaxis results of neutrophils in the chemotactic model adopted by the method in this embodiment have been used to establish accurate analysis indicators, and the indicators were as follows.

1. Chemotaxis Distance (CD): the farthest distance that neutrophils can reach in two hours of chemotactic movement in the agarose chemotactic model, which was greater than or equal to 1755.85 μm.

2. Chemo Cell Ratio (CCR): the percentage of the number of completely chemotactic cells in the total number of chemotactic cells ($10^5$), which was greater than or equal to 3.34%. The percentage was calculated as follows:

CCR=(the number of completely chemotactic cells/the total number of chemotactic cells)×100%.

3. Chemo Index (CI): the ratio of the number of chemotactic cells in zone I and zone II to the total number of chemotactic cells, which was greater than or equal to 39.63, and the ratio was calculated as follows:

CI=[(the number of chemotactic cells in zone $I$+the number of chemotactic cells in zone $II$)/the total number of chemotactic cells]×100%.

4. Maximum Speed of Chemotaxis (Vmax): the ratio of the farthest distance that neutrophils can reach in two hours of chemotactic movement to the chemotaxis time (120 min), which was greater than or equal to 14.63 um/min, and was calculated as follows:

Vmax=chemotaxis distance/chemotaxis time=CD/120.

In conclusion, through the centrifugation and lysis of the blood sample, neutrophils can be quickly obtained, the extraction speed can be improved, and the detection time can be shortened. The method is simple, efficient and fast, and the extracted neutrophils have improved properties.

The invention claimed is:

1. A method for detecting chemotaxis of neutrophil, comprising the following steps:
   i, collecting a blood sample into an Ethylenediaminetetraacetic acid (EDTA) anticoagulant tube, adding an equal volume of glucose, mixing, and standing;
   ii, taking a supernatant of the blood sample after standing into a centrifuge tube, and centrifuging;
   iii, adding 1× calcium and magnesium ion-free Hank's balanced salt solution into a centrifuged blood sample to re-suspend cell aggregates at a bottom thereof;
   iv, uniformly blowing and dispersing re-suspended bottom cell aggregates, and slowly adding a polysucrose solution from a bottom of the centrifuge tube to perform density gradient centrifuging treatment;
   v, dividing a density gradient centrifuged solution into three layers, pipetting a clear liquid at an upper layer and a peripheral blood mononuclear cell (PBMC) layer at a middle layer to obtain cell aggregates at a bottom layer;
   vi, lysing erythrocytes in the cell aggregates by using sterile water, gently blowing and sucking, then successively adding 2× calcium and magnesium ion-free Hank's balanced salt solution and 1× calcium and magnesium ion-free Hank's balanced salt solution, mixing, and centrifuging again to obtain neutrophils; and
   vii, counting the neutrophils, adjusting concentration of the neutrophils, and pipetting a neutrophil suspension into a chemotactic model to chemotactic move.

2. The method for detecting chemotaxis of neutrophil according to claim 1, wherein, step ii specifically comprises:
   letting the blood sample stand still at room temperature for 20 minutes, taking the supernatant of the blood sample into the centrifuge tube, and centrifuging the supernatant at a centrifugal force of 400 g and 20° C. for 10 minutes.

3. The method for detecting chemotaxis of neutrophil according to claim 1, wherein, in step iv, the density gradient centrifuging treatment specifically comprises:

centrifuging at a centrifugal force of 400 g and 20° C. for 35 minutes.

4. The method for detecting chemotaxis of neutrophil according to claim 1, wherein the erythrocytes in the cell aggregates need to be lysed twice.

5. The method for detecting chemotaxis of neutrophil according to claim 1, wherein in step vi, said centrifuging again specifically comprises:

centrifuging at a centrifugal force of 400 g and 20° C. for 7 minutes.

6. The method for detecting chemotaxis of neutrophil according to claim 1, wherein the chemotaxis model is a culture dish, and the culture dish is a transparent culture dish to observe a migration of neutrophils.

\* \* \* \* \*